United States Patent [19]

Gutentag

[11] Patent Number: 4,505,679
[45] Date of Patent: Mar. 19, 1985

[54] ENDODONTIC SEALING APPARATUS AND METHOD

[76] Inventor: Herbert N. Gutentag, 200 Maple Ave., Red Bank, N.J. 07701

[21] Appl. No.: 507,972

[22] Filed: Jun. 27, 1983

[51] Int. Cl.³ .............................................. A61C 5/02
[52] U.S. Cl. .................................................. 433/224
[58] Field of Search ...................... 433/224, 227, 136; 215/260, 270, 358

[56] References Cited

U.S. PATENT DOCUMENTS 1,039,268  9/1912  Gadue .................................. 215/270
4,400,160  8/1983  Lustig et al. ......................... 433/224

Primary Examiner—Robert Peshock
Attorney, Agent, or Firm—Arnold D. Litt

[57] ABSTRACT

The invention relates to a flexible diaphragm which is surrounded at its periphery by an annular ring. This diaphragm is implanted into the pulp chamber after endodontic treatment and provides a covering for the root canal system to prevent infiltration of bacteria and other sources of infection. The device finds particular utility in the context of post-operative inflammation and/or infection in the supporting tissues which may result in build up of intraosseous pressure. The flexibility of the diaphragm material permits it to expand under pressure, thereby minimizing any discomfort which may be otherwise experienced by the patient.

4 Claims, 5 Drawing Figures

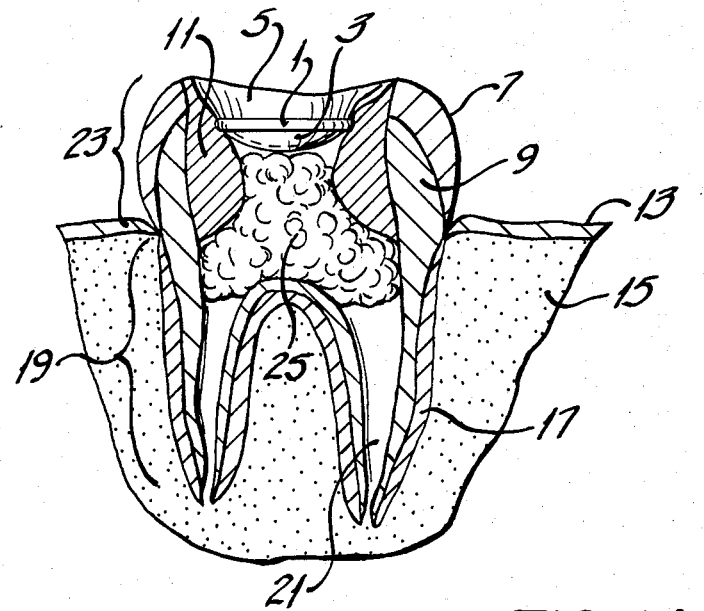
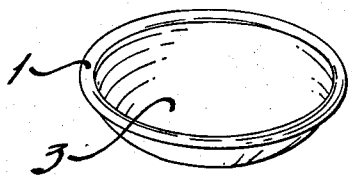
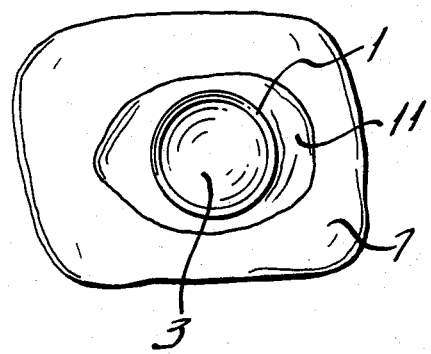

ENDODONTIC SEALING APPARATUS AND METHOD

BACKGROUND OF THE INVENTION

This invention relates to a protective sealing device utilized in the field of dentistry called endodontics which deals primarily with root canal therapy. The root of the tooth is usually comprised of one major canal and a variable number of accessory or auxiliary canals which communicate with the major root canal and with the supporting tissues surrounding the tooth. In order to obtain a complete and successful therapy on the tooth, it is necessary that the primary root canal be properly sealed during the healing process to prevent bacterial infection in the treated area of the tooth.

The instant invention specifically relates to an apparatus which will temporarily seal the root canal area with minimum discomfort to the patient, during the healing process and the process of inserting same in the root canal area.

DESCRIPTION OF THE PRIOR ART

The prior art generally teach the use of medicated cotton pellets which are inserted in the root canals after they have been cleansed. The cotton pellets are kept in place by way of a cement which is temporary in nature. They are usually treated preliminarily with an anti-bacterial compound to prevent infection. However, these prior art processes can be quite painful during the healing process. This is so since in many cases inflammation may generate substantial pressure and pain to the patient.

Since the cement has no flexibility, the patient may have to return to the dentist to have the cement removed in order to allow a decrease in the pressure which has built up, in an effort to ease the pain experienced by the patient. The use of non-flexible sealant devices for the purpose indicated above is taught in such references as U.S. Pat. No. 1,335,413 issued Mar. 30, 1920 to James Herman Abbott, wherein a non-flexible cup is disclosed. The non-flexible cup is inserted into the tube and held in place by surrounding it with gutta percha or cement. Unfortunately, this process suffers from the same disadvantages as other prior art systems, in that the rigid cement can lead to pressure build up within the tooth cavity thereby generating pain to the patient.

By virtue of the instant invention, a flexible device is provided which is easily inserted into the tooth cavity after the endodontic technique, and, by virtue of its flexible nature, reduces pain associated with pressure build up, thereby avoiding the difficulties encountered by prior art system.

SUMMARY OF THE INVENTION

In order to reduce the severity and frequency of post-operative pain after biomechanical instrumentation and/or closing a previously open and draining tooth, a flexible protective sealing device is provided, helpful in enhancing the healing process.

In the normal endodontic procedure usually under a local anesthetic an access opening is made into the pulp chamber using a high speed drill under water coolant. No matter whether the pulp is vital or non-vital, infected or inflamed, the first objective is to debride the remaining pulp tissue from the canals completely to the root apex. Biomechanical instrumentation of the root canals is usually accomplished with root canal files and reamers in conjunction with various irrigation solutions (e.g. saline, sodium hypochlorite, water, or anesthetic solutions). Upon completion of the cleaning phase of treatment, the canals are dried, medicated and sealed to the exterior tooth surface with a temporary cement.

The final objective of root canal treatment is to three-dimensionally fill and seal the canals. The sealing of root canals is most commonly done with gutta percha coated with a cement utilizing the lateral condensation method well known in the art. Other methods are used with success as well, including: the warm gutta percha technique, Sargenti's N2 method and the McSpadden compactor technique.

The sealing device of the instant invention serves to prevent bacterial infection through blockage of bacterial entry into the canal and to prevent entry of other foreign debris into the canal area. It also serves to reduce pain in the patient due to build up of intraosseous pressure, as a consequence of the unique design of the device.

The present device relates to a non-rigid, flexible, expandable membrane which is surrounded at its periphery by a metallic ring or other suitable material (e.g. plastic) to provide a supportive member at the periphery, in one embodiment of the invention. The diaphragm itself may comprise any flexible material which is compatible with the tooth such as, for example, rubber, synthetic rubber products or elastic polymers.

In a preferred embodiment, a rubber diaphragm is utilized. The diaphragm is secured at the periphery of the ring by way of cement. The rubber, being flexible, has the ability to expand in the event of inflammation and resulting pressure build up in the interior of the tooth. Thus, in the event of inflammation or infection, the diaphragm can "give? thereby eliminating to a large degree the pain otherwise experienced by the patient during the healing process of root canal work.

The rubber membrane is characterized by being resistant to the passage of fluids, gases and bacteria which might otherwise infiltrate the area. Rubber dams presently utilized by dentists as material to cover certain areas in the mouth in isolating an operating site may comprise the membrane. Rubber, e.g. latex, can also be used in the context of the instant invention.

In another embodiment of the invention, the sealing device comprises an hourglass-shaped structure. It is characterized by having a flexible orifice and is tubular at one end, flanging to a funnel at the other end. This could be utilized in lieu of the first embodiment described herein above. The hourglass shaped sealing device has distinct advantages over the first embodiment of the invention in that it will better withstand biting forces; will provide a better seal by virtue of allowing the temporary cement to seal and interlock around the exterior of the hourglass-shaped member. Any other geometrical structure which will fit easily within the root canal area can be utilized. The essence of the invention lies in the flexibility of the material which will expand in the event inflammation and build up of pressure inside the root canal, takes place.

A clearer understanding of the nature of the sealing device utilized herein may be obtained upon a review of the accompanying drawings.

BRIEF DESCRIPTION OF THE DRAWINGS

FIG. 1 is a sectional view showing the root canal of a tooth with one embodiment of the sealing device in place.

FIG. 1A depicts the sealing device shown in FIG. 1.

FIG. 2 is a top view of the tooth with the sealing device, shown in this perspective as a ring, in place.

DESCRIPTION OF THE PREFERRED EMBODIMENTS

In FIG. 1, a sectional view of the tooth shows the implantation of the annular device. A metallic ring, 1, surrounds the periphery of the flexible membrane constituting the diaphragm, in this embodiment comprising a rubber dam, 3. The rubber shows a slight concavity. After the endodontic treatment, medicated cotton pellets, 25, are placed over the orifices of the root canal, 21. The medication helps prevent infection of the periapical bone, 15. The enamel of the tooth is depicted as 7, dentin, 9, and the cementum, as 17. The root is shown as 19, the gingiva as 13, and the crown as 23.

After the medicated cotton pellets are inserted into the root canal, the annular dam is inserted as indicated and held in place by a slight application of temporary cement, 11, (e.g. cavit G). The cement adheres to the metallic ring, attaching it in turn to the dentin enamel. The cement and tooth surface on the posterior side of the device is designated, 5. In the event there is inflammation which results in an interior pressure build up, the flexible dam reacts to the pressure in an outward manner, in essence, expanding, much like the action of a balloon. This relieves pressure build up and results in continued comfort to the patient.

The ring may comprise any suitable material such as metal (e.g. stainless steel, carbide, copper), rubber, synthetic rubber products, elastic polymers or plastic and the like.

The dam or membrane itself may comprise any flexible, non-rigid material compatible with the tooth structures including but not limited to the following: rubber, synthetic rubber products or elastic polymers and the like. Implantation of the annular device is done by any of the well known surgical implantation techniques utilized in endodontic dentistry.

The concavity of the flexible membrane is shown clearly in FIG. 1A.

FIG. 2 is a top view looking down at the tooth. In this occlusal view, the metallic ring, 1, is shown at the periphery of the rubber dam, 3, the annular device held in place by cavit G cement, 11. While cavit G cement is a preferred material, any other material well known in the art may be used such as the following: zinc oxide and eugenol cement, IRM cement or polycarboxylate cement (e.g. Durelon).

Figure 3:
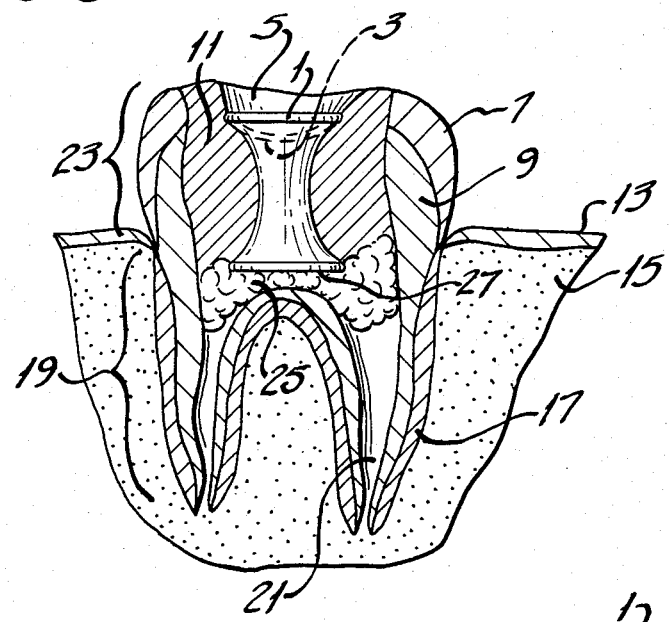
FIG. 3 is a side view of the funnel configuration inserted in the root canal.
Figure 3A:
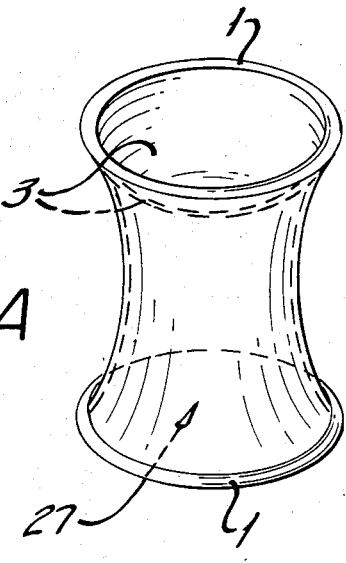
FIG. 3A depicts the funnel configuration shown in FIG. 3.

In FIG. 3 another embodiment of the invention is shown. In this side view, the device takes the form of an hourglass, 4, comprising a ring, 1, at the periphery of the rubber dam, 3. As in the first configuration, the rubber has a slight concavity. Extending down from the sides of the metallic ring is a substantially rigid member which provides an enclosure within which the rubber dam extends. The rigid member tapers down to a narrow point, then flanges to a wider opening, 27, at the lower end. The hourglass device is essentially hollow throughout in the space below the rubber dam.

Preferred lengths for the device range from 4 to 5 millimeters, although lengths ranging from 1 to 10 millimeters are satisfactory. The diameters of the orifice may range from 2 to 5 millimeters although openings ranging from 1 to 15 millimeters are satisfactory.

The advantages of the hourglass device over the more shallow annular device include the following: better withstanding of biting forces; provision of a better seal by virtue of allowing the temporary cement to seal and interlock around the exterior of the funnel.

The medicated cotton pellets do not form a part of this invention and such packing procedure is well known in the literature, (Grossman, L. I., Endodontic Practice, 10th Edit.; Ingle, J. I., Beveridge, E. E., Endodontics, 2nd Edition). While such medication helps to prevent possible infection and reduce inflammatory responses, some inflammation may be an inevitable by-product of the bio-mechanical aspects of endodontic treatment. It is evident that the sealant apparatus finds an advantage in such treatment particularly related to its expandability which results in greater comfort to the patient during the healing process.

After the healing process is completed, the device is easily removed by loosening the cement surrounding the device thereby dislodging the apparatus and facilitating its easy removal.

Having thus described the invention, what is claimed is:

1. A sealing device for insertion into a root canal tooth for temporarily sealing said root canal comprising an hourglass-shaped device consisting of an orifice comprising a rim from which extends a flexible material therefrom forming a slight concavity; and wherein a substantially rigid hollow, hourglass-shaped member extends from said rim providing an enclosure within which said flexible material extends, said hourglass-shaped member tapering to a narrower orifice relative to the initial opening, and wherein said narrower orifice then widens to form a second opening which fits over the entrance to the root canal.

2. The sealing device of claim 1 wherein said rim and said hourglass-shaped member are comprised of a rigid material, selected from the group consisting of stainless steel, carbide or copper.

3. The sealing device of claim 1 wherein the flexible material comprises rubber, rubber-like products or elastic petroleum by-products.

4. The temporary sealant of claim 1 comprising cavit G.

* * * * *